United States Patent
Rosini et al.

(10) Patent No.: US 9,943,540 B2
(45) Date of Patent: Apr. 17, 2018

(54) PHARMACEUTICAL FORMULATION FOR THE TREATMENT OF OSTEOARTHRITIS CONTAINING CLODRONIC ACID AND HYALURONIC ACID

(71) Applicant: ABIOGEN PHARMA S.P.A., Ospedaletto (IT)

(72) Inventors: Sergio Rosini, Ospedaletto (IT); Silvia Trasciatti, Ospedaletto (IT)

(73) Assignee: ABIOGEN PHARMA S.P.A., Ospedaleto (IT)

( * ) Notice: Subject to any disclaimer, the term of this patent is extended or adjusted under 35 U.S.C. 154(b) by 0 days.

(21) Appl. No.: 14/476,521

(22) Filed: Sep. 3, 2014

(65) Prior Publication Data

US 2014/0371170 A1 Dec. 18, 2014

Related U.S. Application Data

(63) Continuation of application No. 12/159,222, filed as application No. PCT/EP2006/012367 on Dec. 21, 2006, now abandoned.

(30) Foreign Application Priority Data

Dec. 29, 2005 (IT) .............. MI2005A2515

(51) Int. Cl.
- *A61K 31/728* (2006.01)
- *A61K 31/663* (2006.01)
- *A61M 5/178* (2006.01)

(52) U.S. Cl.
CPC .......... *A61K 31/728* (2013.01); *A61K 31/663* (2013.01); *A61M 5/178* (2013.01)

(58) Field of Classification Search
None
See application file for complete search history.

(56) References Cited

FOREIGN PATENT DOCUMENTS

EP 0203649 12/1986

OTHER PUBLICATIONS

West, D.C. et al. "Angiogenesis Induced by Degradation Products of Hyaluronic Acid." et al. Science, vol. 328, pp. 1324-1326. 1985.
Sattar, A. et al. "Application of Angiogenic Oligosaccharides of Hylaluronan Increases Blood Vessel Numbers in Rat Skin." J. Invest. Dermatol., vol. 103, pp. 576-579. 1994.
Bernardeau, C. et al. "Acute arthritis after intra-articular hylauronate injection: onset of effusions without crystal." Ann. Rheum. Dis., vol. 60, pp. 518-520-. 2001.
Puttick, M.P.E. et al. "Acute Local Reactions after Intrarticular Hylan for Osteoarthritis of the Knee." J. Rheum. Dis., vol. 60, pp. 1311-1314. 1995.
Magilavy, D. et al. "A Local Reaction to the Intra-Articular Hylan G-F 20 (Sunvisc): Part I-II." Letters to the Editor. J. Bone Joint Surgery. Am., vol. 85(5), pp. 967-969. 2003.
Roth, A. et al. "Intra-articular injections of high-molecular-weight hyaluronic acid have biphasic effects on joint inflammation and destruction in rat antigen-inducted arthritis." Arthritis Research and Therapy., vol. 7, pp. R677-R686. 2005.
Leopold, S. S. et al. "Increased Frequency of Acute Local Reaction to Intra-Articular Hylan GF-20 (Synvisc) in Patients Receiving More Than One Course of Treatment." J. Bone. Joint. Am., vol. 84(9), pp. 1619-1623. 2002.
Bellamy, N. et al. "Evaluation of WOMAC 20, 50, 70 response criteria in patients treated with hylan G-F 20 for knee osteoarthritis." Ann. Rheum. Dis. vol. 64 pp. 881-885. 2005.
International Search Report dated May 16, 2007 for PCT/EP2006/012367 filed on Dec. 21, 2006 in the name of ABIOGEN PHARMA SPA.
Written Opinion dated May 16, 2007 for PCT/EP2006/012367 filed on Dec. 21, 2006 in the name of ABIOGEN PHARMA SPA.

*Primary Examiner* — Shaojia A Jiang
*Assistant Examiner* — Bahar Craigo
(74) *Attorney, Agent, or Firm* — Silvia Salvadori, P.C.; Silvia Salvadori

(57) ABSTRACT

Disclosed are pharmaceutical compositions containing clodronic acid and hyaluronic acid or their salts as active constituents, mixed with suitable vehicles.

10 Claims, No Drawings

PHARMACEUTICAL FORMULATION FOR THE TREATMENT OF OSTEOARTHRITIS CONTAINING CLODRONIC ACID AND HYALURONIC ACID

CROSS REFERENCE TO RELATED APPLICATIONS

This application is a US Continuation Application of Ser. No. 12/159,222 filed on Jun. 26, 2008, which, in turn, claims priority to PCT/EP2006/012367 filed on Dec. 21, 2006 which, in turn, claims priority to Italian application No. MI2005A002515 filed on Dec. 29, 2005 and are incorporated herein by reference in their entirety.

This invention relates to pharmaceutical formulations containing hyaluronic acid and clodronic acid or their salts, especially their sodium salts, as active constituents.

Osteoarthritis (OA) is a progressive chronic illness which particularly affects the joints most subject to mechanical stresses, such as the hips and knees. When this condition arises, the whole joint is affected by a series of degradation and repair processes which eventually alter the anatomy and function of the joint, affecting all the joint components such as the cartilage, subchondral bone and synovial tissues. OA is therefore the result of a set of interrelations between systemic factors (e.g. advanced age or obesity) and local factors (e.g. trauma or excessive use) which are modulated in turn by numerous predisposing factors, possibly combined with infectious and inflammatory events with various aetiologies. In the past, the cartilage was considered to be responsible for OA, and its only target. However, extensive evidence has recently been obtained that the subchondral bone may be the pathogenetic factor responsible for the onset and progress of OA.

In this complex of events, attempts have been made over the years to treat the condition by combating the individual causal processes and using local or systemic anti-inflammatory drugs or intra-articular injections of hyaluronic acid. More recently, the use of drugs which affect the bone metabolism, such as bisphosphonates, has been suggested. Limited use has also been made of some drugs described, more or less arbitrarily, as chondroprotectors (anthraquinones, chondroitin sulphate, etc.), but their real curative capacity is very low and controversial.

In particular, bisphosphonates are well known substances for inhibiting bone resorption and are used in the treatment of postmenopausal osteoporosis, Paget's disease, and tumour osteolysis.

Nevertheless, in a study on rats conducted by the Applicant, sodium clodronate, which belongs to the category of bisphosphonates, proved able to inhibit damaging effects on the joint structures by Freund's adjuvant, which suggests a possible use in joint disease, especially gonarthritis and coxarthritis, in view of its effects on the inflammatory cytokines, its inhibiting effect on the macrophages and the production of metalloproteases, and its stabilising effect on the subchondral bone. In another study on patients with synovitis secondary to knee osteoarthritis, clodronate treatment determined a significant improvement of patient's symptomatology (R. Cocco et al.—, J. Biol. Res., 1999 September N. 11-12-Vol LXXV) suggesting a possible role of bisphosphonate in the treatment of osteoarthritis.

EP 0203649 discloses the use of clodronic acid at the concentration from $10^{-1}$ to $10^{-6}$ M for the preparation of a medicament to be administered intra-articularly for the treatment of osteoarthritis.

During a clinical trial performed by the Applicant with a bisphosphonate (sodium clodronate) for intra-articular use in patients suffering from evident gonarthritis, interesting results were observed after 5 intra-articular injections of 2 mg of sodium clodronate in terms of attenuation of pain and recovery of joint movement.

Furthermore, during an official multicenter clinical study sponsored by the Applicant to assess the effectiveness of intra-articular administration of clodronate in patients affected by gonalgia and gonarthrosis, the best responses were obtained after intra-articular injection of 2 mg of clodronate supplied once a week over 4 consecutive weeks.

However, in addition to these favourable results, some adverse events were also observed, such as a pain response at the time of the injection due to the excessive acidity of the clodronate solution. The low pH used was dictated by stability problems, +which made less acid values of the solutions unacceptable.

Another important product used for OA is hyaluronic acid in its various forms with different molecular weights. Hyaluronan products include Hyalgan® (sodium hyaluronate, molecular weight [MW] 500-730 kDa), Supartz® (sodium hyaluronate, MW 630-1170 kDa), Artz® (sodium hyaluronate, MW 700-1,200 kDa) and others of higher molecular weight (MW from 1100 to 6000 kDa) such as Orthovisc® (MW 1100-2900), Nuflexxa® (MW 2400-3500 kDa) and Synvisc® (hylan G-F 20, approx MW 6000 kDa).

Sodium hyaluronate (MW 500-730 kDa) is administered as three or five weekly 2 ml, 10 mg/ml injections (Hyalgan—Prescribing Information. NY Sanofi-Synthelabo Inc. 2001); similarly sodium hyaluronate (MW 630-1170 kDa; 700-1200 kDa) is administered as a weekly 2.5 ml, 10 mg/ml injection for 5 weeks (Supartz—package insert; Seikagaku Corporation 2001; Artz—Prescribing Information) and higher molecular weight hyaluronans are employed as at least three to five weekly 2 ml, from 8 to 25 mg/ml (M. Pagnano, G. Westrich; Osteoarthritis and Cartilage (2005), 13, 751-761; L. Stefan et al. *Ann Rheum Dis,* 1996, 55:424-431).

The intra-articular application of hyaluronic acid involves not only some interference with the synovial cells, but also a mechanical effect of lubrication of the cartilage structures. Its efficacy in the relief of pain and improvement in joint function has been shown in numerous clinical studies.

However, it was observed that oligosaccharide fragments of hyaluronic acid deriving from the degradation activity of the endogenous enzyme hyaluronidase also posses an angiogenetic action as well as stimulating the production of proinflammatory cytokines (TNFα and IL-1 β) by the macrophages (M. Fiorini et al.—, Rivista Italiana di Tissue Banking 51-52; D. C West et al.—, Science 1985, 228:1324-1326; A. Sattar et al.—J. Invest Dermatol, 1994, 103:576-9), events which can occur after the intra-articular application of hyaluronic acid and that can certainly be harmful to a cartilage if not suitably counteracted.

In practice, despite some favourable effects found with the clinical use of hyaluronic acid, it does not intervene in the degenerative processes affecting the subchondral bone and it has been found eventually cause inflammation and cartilage damage, (C. Bernardeauc et al.—Ann Rheum Dis 2001, 60:518-520; M P Puttick et al.—, J Rheumatol. 1995 July; 22(7):1311-4; D. Magilavy et al.—, J. Bone Joint Surg. Am. 2003 85(5):967-969) especially in long-term and/or repeated courses of treatment (A. Roth et al.—, Arthritis Research and Therapy 2005, 7:R677-R686; Seth S. et al.—, J. Bone Joint. Am., 2002 September 84(9):1619-1623).

Moreover, for hyaluronic acid to perform its protective action, repeated i.a. administrations (at least 3, but more frequently 5 or more injections at short intervals) are required, obviously resulting in low compliance by patients and the risk of problems associated with this practice, which is not easy to perform.

It has now surprisingly been found that a solution of sodium clodronate in hyaluronic acid, at low concentrations, gives better results in a shorter time than the individual products. The formulations according to the invention have also enabled lower concentrations of sodium clodronate than usual to be used, thus reducing the side effects associated with the acidity of the compound and advantageously reducing the number of administrations. At the same time, sodium clodronate, thanks to its pharmacological properties, counteracts any adverse effects of i.a. administration of hyaluronic acid as a consequence of the angiogenetic and stimulatory activity of the macrophagic production of cytokines induced by oligosaccharide fragments of HA, and also allows a reduction in the number of hyaluronic acid administrations. Furthermore, in case of serious OA which necessarily requires high clodronate concentration, the present formulation, thanks to the buffered and masking effect of hyaluronic acid, permits the administration of clodronate thus reducing the pain commonly related to intra-articular administration. The formulations of invention therefore surprisingly represent a new improved solution for the treatment of OA which is particularly advantageous in terms of efficacy, compliance and reduction of adverse effects compared with the prior art.

Thus, the object of the present invention is a pharmaceutical composition comprising clodronic acid and hyaluronic acid or their salts as active ingredients.

The sodium clodronate concentration can range between 0.5 mg and approx. 1.5-2.0 mg. The preferred concentration is 1 mg/ampoule in 1 or 2 ml of hyaluronic acid. Higher doses of clodronate (approx 3-5 mg) can be used, provided that they are suitably buffered with appropriate amounts of hyaluronic acid. Said amounts can reasonably range between 5 and 30 mg/ampoule and final volumes of between 0.5 and 5.0 ml, to be used according to the joint affected.

Hyaluronic acid in all its different forms with different molecular weights (MW from $0.4\times10^3$ kDa to approx $6\times10^3$ kDa) as known from the present prior art or which could be developed in the future can be used to perform the present invention. Preferred hyaluronic acids or sodium salt thereof are those with a molecular weight (MW) of between 0.4 and $1.5\times10^3$ kDa.

Sodium clodronate and sodium hyaluronan solutions generally have a pH of between 4.8 and 6.0.

A preferred solution of the invention consists in a composition of 1 mg of sodium clodronate in 1 or 2 ml of hyaluronic acid sodium salt, with a molecular weight of approx $0.6\times10^3$ kDa (10-20 mg).

A further preferred solution of the invention consists in a composition of 3 mg of sodium clodronate in 2-3 ml of hyaluronic acid sodium salt, with a molecular weight of approx $0.9\times10^3$ kDa (25 mg).

The compositions according to the invention may contain the usual preservatives, especially for the formulation of the combined product in disposable syringes.

Preliminary clinical trials with the formulations according to the invention were based on the measurement of Womac 20 and Womac 50, ie. a 20% and 50% improvement in the symptoms to establish the responders to the treatment (Ann Rheum Dis. 2005). Recently, to assess the effectiveness of intra-articular clodronic acid, 1 mg of clodronic acid is administered in patients with gonarthritis obtaining an improvement in symptoms which, when evaluated with Womac 50, related to 32% of the patients.

The invention is illustrated in more detail in the following example.

EXAMPLE 15 patients suffering from gonarthritis received, according to the invention, an infiltration of 2 ml of solution constituted by 20 mg of hyaluronic acid (Hyalgan) together with 1 mg of clodronic acid once a week for 3 weeks.

At the end of the infiltration cycle, as reassumed in the following table, 58% of the patients were responders according to Womac 20, and 37% were responders according to Womac 50.

These results were better than the equivalent infiltration cycle performed with the individual drugs; Womac 20 was 41% and 43% and Womac 50 was 24% and 27% for hyaluronic acid (20 mg/2 ml) and clodronic acid respectively (1 mg in 2 ml of buffered placebo solution).

The final result of 3 weekly infiltrations of the combination of the two drugs was also better than the cycle with 5 weekly infiltrations of hyaluronic acid (Womac 20:51% and Womac 50:30%) or clodronic acid (Womac 20:54% and Womac 50:32%).

TABLE

| Treatment | | | | | |
|---|---|---|---|---|---|
| type | time | volume of the injected solution | total quantity of drug at end of treatment | Womac 50 | Womac 20 |
| Sodium hyaluronate (20 mg) + clodronic acid (1 mg) | once a week for 3 week | 2 ml | sodium hyaluronate: 60 mg clodronic acid: 3 mg | 37 | 58 |
| Sodium hyaluronate (20 mg) | once a week for 3 week | 2 ml | sodium hyaluronate: 60 mg | 24 | 41 |
| Clodronic acid (1 mg) | once a week for 3 week | 2 ml | clodronic acid: 3 mg | 27 | 43 |
| Sodium hyaluronate (20 mg) | once a week for 5 week | 2 ml | sodium hyaluronate: 100 mg | 30 | 51 |
| Clodronic acid (1 mg) | once a week for 5 week | 2 ml | 5 mg | 32 | 54 |

The invention therefore improved efficacy as measured by both Womac 20 and Womac 50.

This finding is particularly surprising in view of the fact that not only the composition of the present invention resolves the symptomatology of a major number of patients, but three weekly administrations are enough to give better results than cycles of five weekly infiltrations of the two substances administered separately. Thus, the composition of the invention resolves the patient's symptomatology also in a shorter time than the two active principles given separately.

Furthermore, in reference to the cycle with 5 weekly infiltrations of hyaluronic acid or clodronic acid administered separately, it should be considered that the composition of the invention gives better response in term of time and number of responders by means a total reduced quantity of each single drug (60 mg of sodium hyaluronate towards 100 mg of the same, and 3 mg of clodronic acid towards 5 mg of the same).

Moreover, the tolerability of the combined treatment was excellent; in particular, no cases of acute microcrystalline arthritis or knee pain were observed in the hours following the injection.

Regard the efficacy and the tolerability of the composition of the invention, in another experimental analysis two patients suffering from severe gonarthritis, as assessed by radiological analysis, received an infiltration of a high clodronic acid concentration (3 mg) together with sodium hyaluronate (Artz) 25 mg/2.5 ml. The patients reported a reduced symptomatology in terms of VAS (pain visual analogue scale; Elsevier 1984—Oxford University Press; 1989) 7 days after the treatment, and also no pain response at the time of the injection which instead normally occurs when clodronate alone is administered intra-articularly, especially at high concentration. Thus, the composition of the invention, thanks to the presence of hyaluronic acid, also allows to administer high concentration of clodronate in patients in need thereof.

Therefore, the composition of the present invention represents an improved solution in terms of efficacy and compliance for the treatment of osteoarthritis (OA). Furthermore, it constitutes a new possible approach of treatment especially for those patients in which separate treatments failed.

The invention claimed is:

1. A method of treatment of osteoarthritis, the method comprising weekly administering by intra-articular route to a subject in need thereof a combination of clodronic acid or its salts and hyaluronic acid or its salts in the form of a pharmaceutical injectable solution comprising 1 mg of clodronic acid or its salts and 20 mg of hyaluronic acid or its salts as the only active ingredients and suitable vehicles, wherein said weekly administration is carried out once a week for three weeks.

2. The method as claimed in claim 1, wherein said pharmaceutical injectable solution is administered through a disposable syringe.

3. The method as claimed in claim 1, wherein the solution comprises sodium clodronate.

4. The method as claimed in claim 1, wherein the solution comprises hyaluronic acid or its salts having molecular weight from $0.4 \times 10^3$ to $6 \times 10^3$ kDa.

5. The method as claimed in claim 4, wherein the solution comprises hyaluronic acid or its salts having molecular weight from $0.4 \times 10^3$ to $1.5 \times 10^3$ kDa.

6. The method as claimed in claim 5, wherein the solution comprises hyaluronic acid or its salts having molecular weight approximately $0.6 \times 10^3$ kDa.

7. The method as claimed in claim 5, wherein the solution comprises hyaluronic acid or its salts having molecular weight approximately $0.9 \times 10^3$ kDa.

8. The method as claimed in claim 1, wherein the solution comprises sodium hyaluronate.

9. The method as claimed in claim 1, wherein the solution comprises sodium clodronate and sodium hyaluronate.

10. The method as claimed in claim 1, wherein the pharmaceutical injectable solution has a total volume of 2 ml.

* * * * *